(12) United States Patent
Farrington et al.

(10) Patent No.: US 6,309,422 B1
(45) Date of Patent: Oct. 30, 2001

(54) BONE GRAFTING MATERIAL

(75) Inventors: Alfred Farrington, 9454 Wilshire Blvd., Suite 311, Beverly Hills, CA (US) 90212; Frank K. Huang, Sunnyvale, CA (US)

(73) Assignee: Alfred Farrington, Beverly Hills, CA (US)

( * ) Notice: Subject to any disclaimer, the term of this patent is extended or adjusted under 35 U.S.C. 154(b) by 0 days.

(21) Appl. No.: 09/242,648

(22) PCT Filed: Jun. 18, 1998

(86) PCT No.: PCT/US98/12605
§ 371 Date: Feb. 19, 1999
§ 102(e) Date: Feb. 19, 1999

(87) PCT Pub. No.: WO98/58602
PCT Pub. Date: Dec. 30, 1998

Related U.S. Application Data
(60) Provisional application No. 60/050,295, filed on Jun. 20, 1997, now abandoned.

(51) Int. Cl.⁷ ..................................................... A61F 2/28
(52) U.S. Cl. ..................................... 623/23.51; 623/23.61; 523/116; 433/228.1
(58) Field of Search .................................. 623/16, 23.61, 623/23.75, 23.76, 23.62, 23.51; 433/199.1, 228.1; 523/116

(56) References Cited

U.S. PATENT DOCUMENTS

| | | | | |
|---|---|---|---|---|
| 3,899,607 | * | 8/1975 | Miller et al. | 426/285 |
| 4,264,493 | * | 4/1981 | Battista | 260/117 |
| 4,869,906 | * | 9/1989 | Dingeldein et al. | 424/423 |
| 4,904,585 | * | 2/1990 | Shimada et al. | 435/88 |
| 5,455,231 | * | 10/1995 | Constantz et al. | 514/21 |
| 5,580,623 | * | 12/1996 | Fulmer et al. | 428/34.1 |

FOREIGN PATENT DOCUMENTS

98/58602 * 12/1998 (WO) ..................................... 623/16

* cited by examiner

*Primary Examiner*—Paul B. Prebilic
(74) *Attorney, Agent, or Firm*—Mitchell, Silberberg & Knupp LLP

(57) ABSTRACT

The application relates to a synthetic bone grafting powder mix comprising a calcium compound and protein. Preferably, the ratio by weight of the calcium compound to protein is between 90:10 to 70:30. Further, the preferred calcium compound comprises one of the following (a) Calcium Phosphate ($Ca_3(PO_4)_2$); (b) Calcium Carbonate ($Ca(CO_3)$); (c) Fluorapatite ($Ca_{10}(PO_4)_6F_2$); (d) Monetite ($CaHPO_4$); or (e) Hydroxyapatite ($Ca_{10}(PO_4)_6(OH)_2$).

16 Claims, No Drawings

BONE GRAFTING MATERIAL

This application is a national stage application of PCT/US98/12605 filed Jun. 18, 1998 which is a continuation-in-part of provisional application Ser. No. 60/050,295 filed Jun. 20, 1997 now abandoned.

BACKGROUND OF THE INVENTION

Field of the Invention

The present invention relates to a challenging aspect of synthetic bone grafting in medicine by developing a material that mimics real bone. Ultimately, the implanted material will either be replaced or incorporated by new, natural bone. Hydroxyapatite, a form of calcium phosphate, can be used as a bone graft, but implantation of this material results in no resorption, a requirement for the incorporation of new, natural bone. Small crystals of calcium phosphate compounds have also been used for this purpose, but the material does not have the structural strength to remain within the site of implantation. It is resorbed too quickly to allow for the incorporation of new bone. Another problem concerning the use of calcium phosphate involves the handling of this material. The handling and shaping of hydroxyapatite and small crystals of calcium phosphate compounds are extremely difficult, because these materials lack malleability, cohesiveness and the ability to adhere to bone surfaces.

Our material can replace hydroxyapatite and small crystals of calcium phosphate as bone grating material. It has cohesiveness, malleability, and structural strength, which are qualities that can improve the task of bone grafting. The malleability allows for medical professionals to handle and shape the material with ease, facilitating bone grafting procedures. The cohesiveness and structural strength of the material increase its chance for success in adhering to the bone defect site, resulting in a higher possibility for new bone to replace or incorporate the bone grating material within the defect site.

SUMMARY OF THE INVENTION

A challenging aspect of synthetic bone grafting in medicine is developing a material that can mimic the normal characteristics of healthy bone. Hydroxyapatite, a form of calcium phosphate, can be used as a bone graft, but implantation of this material results in no resorption, a requirement for the incorporation of new, natural bone. Small crystals of calcium phosphate compounds have also been used for this purpose, but the material does not have the structural strength to remain within the site of implantation. It is resorbed too quickly to allow for incorporation of new bone. Another problem concerning the use of pure calcium phosphate involves the handling of this material. The handling and shaping of hydroxyapatite and small crystals of calcium phosphate compounds is extremely difficult, because these materials lack cohesiveness and the ability to adhere to bone surfaces.

Implantation of calcium phosphate that contains protein could promote new bone growth by allowing the body to digest the protein away and build a cavernous system within the material. In addition, calcium phosphate that contains protein has greater structural strength than any calcium phosphate compound without protein, allowing the material to stay within the defect long enough for the body to proceed with natural bone replacement.

This document describes a material that incorporates any calcium containing compound and a protein. The protein provides the strength, elasticity, and malleability of the material. It also allows for the body to resorb and replace the protein with its own pre-bone materials and use the calcium compound within the bone grafting material to deposit natural bone. Any protein can be used, although vegetable protein is preferred, such as gluten, glutenin or gliadin. Combinations of different proteins can also be used.

BRIEF DESCRIPTION

The material of the synthetic bone graft is a mixture that contains specific amounts of any form of any calcium containing compound and protein. Vegetable protein is preferred, such as gluten, glutenin and gliadin, or a combination thereof. Adding water to the mixture results in the formation of a protein matrix which incorporates the calcium containing compound. This material could be used as a bone graft for periodontal, jaw, and other bone defects.

DETAILED DESCRIPTION OF THE PREFERRED EMBODIMENT(S)

The synthetic, bone-graft material has the following composition:

a). 90–70% w/w any physical form of any calcium containing compound such as:
   Calcium Phosphate ($Ca_3(PO_4)_2$)
   Calcium Carbonate ($Ca(CO_3)$)
   Fluorapatite ($Ca_{10}(PO_4)_6F_2$)
   Monetite ($CaHPO_4$)
   Hydroxyapatite ($Ca_{10}(PO_4)_6(OH)_2$) etc.
   (90–70% of a mixture of any such compounds could also suffice).

b). 10–30% w/w of protein, preferably vegetable protein (such as gluten, glutenin, and/or gliadin, or a mixture thereof.

c). 40–60% v/w (cc/g) water or other fluid.

The above materials can be put in a bowl or other recepticle and mixed together. There is no particular order in which the materials should be introduced into the mixture. In addition, a portion of the materials can be mixed together with the remaining material mixed in after.

This composition produces a material that is pasty and has moderate cohesiveness and elasticity. By changing the above composition, you can alter the elasticity and hardness of the material, as needed. The material can also been made in powder form by eliminating the water or other fluid. The powder can be applied directly to the bone defect, as can the material which comprises water or other liquid.

Calcium phosphate materials have been known to enhance bone regeneration when implanted into a bone defect site. (See, A. N. Cranin, G. P. Tobin, and J. German, *Compend. Contin. Educ. Dent.*, 1987, 8:334; R. Z. Legeros, *Adv. Dent. Res.*, 1988, 2:164; and K. deGroot, *Bioceramics of Calcium Phosphate*; CRC Press, Inc., Boca Roton, 1983.) Gluten is wheat protein that is available commercially as a food product. It is extracted and milled from wheat flour and contains two subunits of wheat protein called glutenin and gliadin. Glutenin has properties that give strength and elasticity to flour dough. (See also, J. R. Whitaker and S. R. Tannenbaum, *Food Proteins*, The Avi Publishing Company, Wesport, 1977.) Gluten or glutenin provides a protein matrix in which a calcium containing compound can be incorporated. The incorporation of a calcium containing compound into gluten or glutenin according to the above composition produces a paste-like material that is malleable into any shape. The material can be used as a bone graft for implantation into a bone defect site, protecting the defect site and enhancing bone regeneration.

In all cases, a bone site can be treated with or without an incision.

(a) The bone grating material described herein can be injected to a site using a syringe without incision;

(b) Said material can be applied to the site using a spatula after incision;

(c) User can apply said material to a site by hand after incision;

(d) Said material can be condensed to a site after incision; and (e) Said material can be prefabricated into any shape or form and delivered and stabilized over the site with or without any cement after incision.

In addition, the calcium compound(s) and protein mixture can be applied after incision in powder form.

Other embodiments of the invention will be apparent to those skilled in the art from consideration of the specification and practice of the invention disclosed herein.

We claim:

1. A synthetic bone grafting powder mix comprising:
   (a) a calcium compound; and
   (b) vegetable protein, wherein the ratio by weight of the calcium compound to vegetable protein is between 90:10 to 70:30.

2. The mix according to claim 1 wherein the calcium compound comprises one of the following:
   (a) Calcium Phosphate ($Ca_3(PO_4)_2$);
   (b) Calcium Carbonate ($Ca(CO_3)$);
   (c) Fluorapatite ($Ca_{10}(PO_4)_6F_2$);
   (d) Monetite ($CaHPO_4$); or
   (e) Hydroxyapatite ($Ca_{10}(PO_4)_6(OH)_2$).

3. The mix according to claim 1 wherein the calcium compound comprises calcium and phosphorous.

4. The mix according to claim 3 wherein the calcium compound includes a plurality of molecules which each have more than one phosphorous atom.

5. A synthetic bone grafting powder mix comprising:
   (a) a plurality of calcium compounds; and
   (b) vegetable protein,
   wherein the vegetable protein comprises glutenin.

6. The mix according to claim 5 wherein the plurality of calcium compounds comprise Calcium Phosphate ($Ca_3(PO_4)_2$) and one of the following:
   (a) Calcium Carbonate ($Ca(CO_3)$);
   (b) Fluorapatite ($Ca_{10}(PO_4)_6F_2$);
   (c) Monetite ($CaHPO_4$); or
   (d) Hydroxyapatite ($Ca_{10}(PO_4)_6(OH)_2$).

7. The mix according to claim 5 wherein the plurality of calcium compounds comprise Calcium Carbonate ($Ca(CO_3)$) and one of the following:
   (a) Fluorapatite ($Ca_{10}(PO_4)_6F_2$);
   (b) Monetite ($CaHPO_4$); or
   (c) Hydroxyapatite ($Ca_{10}(PO_4)_6(OH)_2$).

8. The mix according to claim 5 wherein the plurality of calcium compounds comprise Fluorapatite ($Ca_{10}(PO_4)_6F_2$) and one of the following:
   (a) Monetite ($CaHPO_4$); or
   (b) Hydroxyapatite ($Ca_{10}(PO_4)_6(OH)_2$).

9. A synthetic bone grafting powder mix comprising:
   (a) a plurality of calcium compounds; and
   (b) vegetable protein,
   wherein the plurality of calcium compounds comprise Monetite ($CaHPO_4$) and Hydroxyapatite ($Ca_{10}(PO_4)_6(OH)_2$).

10. A synthetic bone grafting powder mix comprising:
    (a) a calcium compound; and
    (b) vegetable protein,
    wherein the vegetable protein comprises gluten.

11. A synthetic bone grafting powder mix comprising:
    (a) a calcium compound; and
    (b) vegetable protein,
    wherein the vegetable protein comprises glutenin.

12. A synthetic bone grafting powder mix comprising:
    (a) a calcium compound; and
    (b) vegetable protein,
    wherein the vegetable protein comprises gliadin.

13. The mix according to claim 5 wherein the mix is combined with a liquid comprising water.

14. A method for making a bone grafting material comprising the following steps:
    (a) putting a calcium compound into a receptacle;
    (b) putting vegetable protein into said receptacle;
    (c) putting liquid into said receptacle; and
    (d) mixing said calcium compound, vegetable protein and liquid,
    wherein the ratio by weight of the calcium compound to vegetable protein is between 90:10 to 70:30.

15. The method according to claim 14 wherein the calcium compound comprises one of the following:
    (a) Calcium Phosphate ($Ca_3(PO_4)_2$);
    (b) Calcium Carbonate ($Ca(CO_3)$);
    (c) Fluorapatite ($Ca_{10}(PO_4)_6F_2$);
    (d) Monetite ($CaHPO_4$); or
    (e) Hydroxyapatite ($Ca_{10}(PO_4)_6(OH)_2$).

16. The method according to claim 14, wherein the vegetable protein is selected from the group consisting of gluten, glutenin and gliadin.

* * * * *